United States Patent [19]

Gilbert et al.

[11] Patent Number: 5,416,235
[45] Date of Patent: May 16, 1995

[54] PREPARATION OF SUBSTITUTED ARYL COMPOUNDS

[75] Inventors: Bruce C. Gilbert; Peter Hanson, both of York; Jason R. Jones, Bolton; Allan W. Timms, South Wirral, all of Great Britain

[73] Assignee: Octel Chemicals Limited, Widnes, United Kingdom

[21] Appl. No.: 146,637

[22] Filed: Nov. 1, 1993

[30] Foreign Application Priority Data

Nov. 5, 1992 [GB] United Kingdom ................ 9223195

[51] Int. Cl.⁶ .................. C07C 253/30; C07C 39/02; C07C 39/04; C07C 69/88
[52] U.S. Cl. .................................. 558/350; 546/286; 546/290; 546/345; 548/366.1; 548/373.1; 548/375.1; 548/541; 548/560; 548/561; 549/61; 549/62; 549/81; 549/474; 549/479; 549/505; 558/423; 558/425; 568/629; 568/716; 568/774; 568/775; 560/67
[58] Field of Search ............... 558/350, 423; 560/67; 568/629, 716, 774, 775

[56] References Cited

U.S. PATENT DOCUMENTS

| | | | |
|---|---|---|---|
| 546,086 | 9/1895 | Bischler | 558/350 |
| 1,879,209 | 9/1932 | Hagenest et al. | 558/350 |
| 1,962,559 | 2/1933 | Hagenest et al. | 558/350 X |
| 3,431,300 | 3/1969 | Rogers et al. | 558/350 X |
| 4,376,080 | 3/1983 | Hamamoto et al. | 558/350 |

FOREIGN PATENT DOCUMENTS 395362  8/1973  U.S.S.R. ............................ 558/350

*Primary Examiner*—Joseph Paul Brust
*Attorney, Agent, or Firm*—Seidel Gonda Lavorgna & Monaco

[57] ABSTRACT

A process for the preparation of aromatic compounds of the general formula I, $$Ar-X \qquad \qquad I$$

in which Ar represents an optionally substituted aryl group and X represents a group OH, Cl, Br or CN, by reaction of an aryl diazoniumsalt of the formula II, $$Ar-N=N^+Y^- \qquad \qquad II$$

in which Ar is as defined above and Y represents a suitable counterion, with water, hydrogen chloride or a salt thereof, hydrogen bromide or a salt thereof, or a cyanide in the presence of a copper(I)salt, characterized in that the copper(I)salt is a copper(I)salt derived from an hydroxy carboxylic acid.

15 Claims, No Drawings

PREPARATION OF SUBSTITUTED ARYL COMPOUNDS

The present invention relates to a process for the preparation of aromatic compounds of the general formula I, Ar—X           I in which Ar represents an optionally substituted aryl group and X represents a group OH, Cl, Br or CN, by reaction of an aryl diazonium salt of the formula II, Ar—N≡N⁺Y⁻           II in which Ar is as defined above and Y represents a suitable counterion, with water, hydrogen chloride or a salt thereof, hydrogen bromide or a salt thereof, or a cyanide in the presence of a copper(I)salt. The invention especially relates to the production of substituted phenols from the corresponding anilines by means of diazotation and hydrolysis. In particular the preparation of 4-fluorophenol is described, a difficult reaction to carry out using conventional techniques.

The preparation of aryl chlorides, aryl bromides and aryl cyanides from the corresponding aryl diazonium salts is well known in the literature. The reaction is usually indicated as the Sandmeyer reaction. The reaction is often carried out by heating aryl diazonium salts with cuprous chloride, cuprous bromide or cuprous cyanide in the presence of hydrochloride acid, hydrobromic acid or an alkali metal salt of hydrogen cyanide respectively.

Also the preparation of phenols by hydrolysis of benzenediazonium ions is well known in the literature. It involves the preparation of diazonium salt, e.g. the diazonium hydrogensulphate by treatment of the aniline hydrogensulphate with sodium nitrite in dilute aqueous sulphuric acid, followed by hydrolysis in more concentrated aqueous sulphuric acid. The temperature of the hydrolysis is maintained at the boiling point of the aqueous acid (by proper adjustment of the concentration of the sulphuric acid) and the phenol formed removed from the reaction medium by means of steam distillation in order to minimise the coupling of the formed phenol with more diazonium salt.

In the production of 4-fluorophenol from 4-fluoroaniline a major problem arises with corrosion of the glass lined vessels by hydrofluoric acid. The hydrofluoric acid is considered to arise by nucelophilic displacement of fluoride from the 4-fluorobenzenediazonium hydrogensulphate. This is not surprising since the diazonium group is one of the most electron withdrawing groups known thereby activating the 4-fluoro group to nucleophilic aromatic substitution. Furthermore, the resulting 4-hydroxybenzenediazonium hydrogensulphate may itself be hydrolysed to hydroquinone and thence by reaction with further diazonium ions to "diazo tars".

The liberation of hydrofluoric acid and production of "Diazo Tars" is of course exacerbated by the high temperatures employed in the reaction. A method which avoids these high temperatures and the liberation of hydrofluoric acid is therefore highly desirable.

It is well known that copper salts may be utilised in the Sandmeyer reaction of substituted anilines to the corresponding chlorides (using copper chloride), bromides (using copper bromide), nitriles (using copper cyanide) and phenols (using copper sulphate). The copper halide or pseudohalide is normally present in the copper (I) oxidation stage. Copper (II) sulphate may be used for the preparation of phenols, aryl chlorides, aryl bromides and aryl cyanides, together with small amounts of a reducing agent such as ascorbic acid to initiate a catalytic cycle. The mechanism of the first stage of the reaction is considered to be the reduction of copper (II) to copper (I) by the reducing agent. The resulting copper (I) subsequently reduces the diazonium ion to produce a phenyl radical and nitrogen. Water ligated to copper (II) is believed to be transferred to the phenyl radical producing the phenol and regenerating copper (I). Thus once the reaction has been initiated the cycle should become truly catalytic in copper.

Unfortunately, the ligand transfer of water from copper (II) to the radical is not efficient and large amounts of copper sulphate have to be utilized. Thus what is in principle a catalytic cycle is not in practice. This has major drawbacks in industrial production both in terms of expense of reagent and effluent treatment costs.

It has now been found that the use of a copper salt of an hydroxy carboxylic acid dramatically improves the preparation of compounds of the general formula I as defined hereinbefore. Organic acids such as citric or tartaric acid are suitable. The amount of copper needed may be significantly reduced. The salt of the copper may be prepared in situ.

The present invention therefore relates to a process for the preparation of aromatic compounds of the general formula I, Ar—X           I in which Ar represents an optionally substituted aryl group and X represents a group OH, Cl, Br or CN, by reaction of an aryl diazoniumsalt of the formula II, Ar—N≡N⁺Y⁻           II in which Ar is as defined above and Y represents a suitable counterion, with water, hydrogen chloride or a salt thereof, hydrogen bromide or a salt thereof, or a cyanide in the presence of a copper(I)salt, characterised in that the copper(I)salt is a copper(I)salt derived from an hydroxy carboxylic acid.

Suitable hydroxy carboxylic acid to be used in the process of the present invention are all organic compounds carrying at least one carboxylic acid group and one hydroxy group. The hydroxy carboxylic acid may contain one or more substituents, e.g. aryl groups, halogen atoms, nitro groups, alkoxy groups, phenoxy groups etc., provided that the substituents do not interfere with the reaction.

Preferably the hydroxy carboxylic acid is a straight or branched carboxylic acid having from 2 to 20 carbon atoms, containing up to four carboxylic acid groups and containing up to four hydroxy groups. More preferably the hydroxy carboxylic acid is a mono, di or tri carboxylic acid having up to 12 carbon atoms and containing up to three hydroxy groups. Still more preferably the hydroxy carboxylic acid is mono or di carboxylic acid having up to 8 carbon atoms, such as tartaric acid, citric acid, malic acid, citramalic acid, lactic acid or gluconic acid, citric acid being especially preferred.

Suitable salts of hydrogen chloride, hydrogen bromide and hydrogen cyanide are water soluble metal salts, especially alkali metal and earthalkali metal salts, preferably alkali metal salts such as sodium and potassium salts.

Suitable groups Ar in the compounds of the general formula I comprise hydrocarbocyclic compounds comprising up to five rings, usually up to four rings, more usually up to three rings. Other suitable aryl groups are heterocyclic groups, especially 5- or 6-membered heterocyclic groups containing one to four of the same or different heteroatoms, especially one or two, such as nitrogen, oxygen and sulphur. Especially suitable are thiophene, pyridine, pyrrole, furan and pyrazole. All these groups may be substituted by one or more substituents. In principle, every known substituent in organic chemistry may be used provided that the groups do not interfere with the reaction. Preferably the optionally substituted aryl group is a phenyl or naphtyl group or a 5- or 6-membered heterocyclic group, optionally substituted by one or more halogen atoms or nitro, cyano, alkyl, haloalkyl, alkoxy, haloalkoxy optionally substituted amino, formyl, alkoxycarbonyl, carboxyl, phenyl or halo- or dihalo-phenyl groups. More preferably the optionally substituted aryl group is a phenyl group, optionally substituted by one or more fluorine, chlorine or bromine atoms or nitro, cyano, $C_{1-6}$ alkyl, $C_{1-6}$ haloalkyl, $C_{1-6}$ alkoxy, $C_{1-6}$ haloalkoxy, optionally substituted amino, formyl, $C_{1-6}$ alkoxycarbonyl, carboxyl, phenyl or halo- or dihalo-phenyl groups.

The group Y in the general formula II is suitably a halide atom or a hydrogensulphate group, a phosphate group, a tetrafluoroborate group or a hexafluorophosphate group. Preferably Y represents a chloride or bromide atom or a hydrogensulphate group. In the case that an aryl chloride is to be prepared Y is preferably a chlorine atom, in the case that an aryl bromide is to be prepared Y is preferably a bromide, and in the case a phenol is to be made Y is preferably a hydrogensulphate.

A particular preferred process according to the present invention is the preparation of aromatic compounds of the general formula I in which X represent an OH group, by reaction of an aryl diazonium salt of the general formula II with water.

The copper(I)salts to be used in the process according to the present invention are suitably commercially available compounds as Cu Cl, Cu Br and Cu CN. Cuprous chloride will usually be used for the preparation of aromatic chlorides, cuprous bromide for the preparation of aromatic bromides, and cuprous cyanide for the preparation of aromatic cyanides. Instead of using copper(I)salts it also possible to start with copper(II)salts, followed by in situ reduction to copper(I)salts. The invention therefore also relates to the processes as described hereinbefore, in which the copper(I)salt is prepared by reduction of a copper(II)salt in situ. Suitable reducing agents are ascorbic acid, ferrous sulphate, hydrazine, bisulphite and titanium(III)chloride. Preferably ascorbic acid is used.

In a preferred embodiment of the invention a copper(II)salt is also present in the reaction mixture. The presence of the copper(II)salts results in improved yields.

In another preferred embodiment of the reaction with reaction is carried out in the presence of a water immiscible organic solvent in which the product of the reaction will dissolve. Suitable water immiscible solvents are alkanes as pentane, hexane, heptane, octane, cyclohexane and methylcyclohexane, halogenated alkanes as dichloromethane, chloroform, tetrachloromethane, trichloroethane and trichloroethene, aromatic solvents as benzene, toluene and xylene, halogenated aromatic solvents as chlorobenzene, ketones as methyl t-butyl ketone, and esters as methyl acetate, ethyl acetate and butyl acetate. A preferred water immiscible solvent is ethyl acetate.

The process of the present invention may be carried out at a temperature between 0° C. and 100° C. It is preferred to carry the reaction out at a temperature between 15° C. and 25° C. In the case of the preparation of 4-fluorophenol no fluoride is liberated from the diazonium ion at that temperature.

It will be appreciated that the invention also relates to aromatic compounds of the general formula 1 as defined hereinbefore whenever prepared by a process as described above.

The invention will now be described in more detail by the following examples.

EXAMPLE 1 a. 4-Fluorobenzenediazonium hydrogensulphate

4-Fluoroaniline (11.2 g; 0.1 mol) was added dropwise into a solution of sulphuric acid (25 g) in water (60 ml) over 10 min. A smooth paste was formed. The mixture was cooled to <5° and a solution of sodium nitrite (7.8 g; 0.11 mol) in water (25 ml) was added dropwise over 0.5 hours while maintaining the temperature at <5° with external cooling. A clear red solution was obtained. The solution was stirred for 0.25 hours to complete the reaction and urea (1.0 g) was added to destroy the excess nitrous acid. The resulting solution was used directly in the next stage.

b. 4-Fluorophenol

Copper sulphate pentahydrate (6.25 g; 0.025 mol) and trisodium citrate dihydrate (14.7 g; 0.05 mol) were dissolved in water (60 ml). Ethyl acetate (150 ml) was added and the two phase mixture vigorously stirred. A few ml of the diazonium solution prepared above was added to the stirred mixture. The reaction was initiated by the addition of a solution of ascorbic acid (1.0 g) dissolved in water (20 ml). The remaining solution had been added, the mixture was allowed to settle and the organic phase separated. The aqueous phase was re-extracted with more ethyl acetate and the combined organic phases washed with a little water. The solvent was removed by evaporation under reduced pressure and the residue purified by means of distillation. The product (9.0 g; 80%) was obtained by b.p. 81°/13 mm. Hg. Fluoride ion in the aqueous liquors could not be detected.

EXAMPLES 2–12

Similarly prepared by the methods cited in Example 1 the following compounds are prepared

| Example | Substituent | b.p. (m.p.) |
| --- | --- | --- |
| 2 | 4-Chloro | (41–43°) |
| 3 | 4-Methoxy | (55–57°) |
| 4 | 4-Methyl | 201–202° |
| 5 | Hydrogen | 181–183° |
| 6 | 4-Nitro | (112–114°) |
| 7 | 4-Cyano | (111–113°) |
| 8 | 4-Ethoxycarbonyl | (116–118°) |
| 9 | 2-Fluoro | 171–173° |
| 10 | 2-Chloro | 175–176° |
| 11 | 2-Methyl | 202–204° |
| 12 | 2-Methoxy | 204–206° |

EXAMPLE 13 (for comparative purposes only)

4-Chlorobenzonitrile

Sodium cyanide (2.94 g; 0.06 mol) was added to water and stirred. Cuprous cyanide (2.7 g; 0.03 mol) was added to the mixture stirred until it became homogeneous. 4-chlorobenzenediazonium tetrafluoroborate (5.66 g; 0.025 mol) in water (10 ml) was added to one portion. The mixture was allowed to react at room temperature. The mixture was extracted by ethyl acetate and the extract analysed by means of gas chromatography which indicated that 4-chlorobenzonitrile had been formed in 75% yield.

EXAMPLE 14

4-Chlorobenzonitrile

The method of example 13 was carried out except that trisodium citrate (0.06 mol) was added after the copper cyanide but before the diazonium salt. The reaction was conducted for 1 hour when a yield of 90.4% was obtained by analysis of the ethyl acetate extract.

EXAMPLE 15

4-Chlorobenzonitrile

Copper (II) nitrate (0.03 mol) and trisodium citrate (0.06 mol) were dissolved in water and the pH adjusted to 9–10 with sodium hydroxide solution. Sodium cyanide (0.06 mol) was added and the mixture stirred. 4-Chlorobenzenediazonium tetrafluoroborate (0.025 mol) was added in one portion. After 10 mins the reaction was adjudged to be complete and analysis by gas chromatography indicated a yield of >90%.

We claim:

1. A process for the preparation of aromatic compounds of the general formula I, $$Ar-X \qquad I$$

in which Ar represents an optionally substituted aryl group selected from the group consisting of phenyl, naphthyl, and 5- or 6-membered heterocyclic groups optionally substituted by one or more of halogen, nitro, cyano, alkyl, haloalkyl, alkoxy, haloalkoxy, optionally substituted amino, formyl, alkoxycarbonyl, carboxyl, phenyl, halo-phenyl, and dihalo-phenyl and X is selected from the group consisting of OH, Cl, Br, and CN, the process comprising the steps of:

reacting an aryl diazonium salt of the formula II, $$Ar-N{\equiv}N^+Y^- \qquad II$$

in which Ar is defined above and Y represents a suitable counterion, with water, hydrogen chloride, hydrogen bromide, hydrogen cyanide, or a water soluble metal salt of hydrogen chloride, hydrogen bromide, or hydrogen cyanide, in the presence of a copper (I) salt of a straight or branched chain hydroxy carboxylic acid containing from 2 to 20 carbon atoms.

2. A process according to claim 1, in which the hydroxy carboxylic acid contains up to 4 carboxylic acid groups and up to 4 hydroxy groups.

3. A process according to claim 2, in which the hydroxy carboxylic acid is a mono, di or tri carboxylic acid having up to 12 carbon atoms and containing up to three hydroxy groups.

4. A process according to claim 1, in which the hydroxy carboxylic acid is tartaric acid, citric acid, malic acid, citriamalic acid, lactic acid or gluconic acid.

5. A process according to claim 1, in which the optionally substituted aryl group is a phenyl group, optionally substituted by one or more fluorine, chlorine or bromine atoms or nitro, cyano, $C_{1-6}$ alkyl, $C_{1-6}$ haloalkyl, $C_{1-6}$ alkoxy, $C_{1-6}$ haloalkoxy, optionally substituted amino formyl, $C_{1-6}$ alkoxycarbonyl, carboxyl, phenyl or halo- or dihalo-phenyl groups.

6. A process according to claim 1, in which Y represents a chloride or bromide atom or a hydrogensulphate group.

7. A process as claimed in claim 6, in which Y represents a hydrogensulphate group.

8. A process according to claim 1, in which an aromatic compound of the general formula I in which X represents an OH group, is prepared by reaction of an aryl diazonium salt of the general formula II with water.

9. A process according to claim 1, in which the copper(I)salt is prepared by reduction of a copper(II)salt in situ.

10. A process as claimed in claim 8, in which the reducing agent is ascorbic acid, ferrous sulphate, hydrazine, bisulfite or titanium (III) chloride.

11. A process according to claim 1, in which also a copper(II)salt is present in the reaction mixture.

12. A process according to claim 1, in which the reaction of the hydroxy carboxylic acid is carried out in the presence of a water immiscible organic solvent.

13. A process as claimed in claim 12, in which the water immiscible solvent is ethyl acetate.

14. A process according to claim 1, in which the reaction of the aryl diazonium salt is carried out at a temperature between 0° C. and 100° C.

15. A process as claimed in claim 14, in which the temperature is between 15° C. and 25° C.

* * * * *